United States Patent [19]
Mühle et al.

[11] 3,931,180
[45] Jan. 6, 1976

[54] SUBSTITUTED 6-HYDROXY PYRIMIDINES

[75] Inventors: Herbert Mühle; Karlheinz Milzner, both of Basel; Fritz Reisser, Therwil, all of Switzerland

[73] Assignee: Sandoz Ltd., Basel, Switzerland

[22] Filed: Mar. 19, 1974

[21] Appl. No.: 452,525

[30] Foreign Application Priority Data
Mar. 23, 1973 Switzerland.................... 4254/73

[52] U.S. Cl. 260/256.4 C; 260/256.4 E; 260/256.5 R
[51] Int. Cl.² ........................................ C07D 239/00
[58] Field of Search ............... 260/256.4 C, 256.5 R

[56] References Cited
UNITED STATES PATENTS

| | | | |
|---|---|---|---|
| 2,754,243 | 7/1956 | Gysin et al................. | 424/200 |
| 3,287,453 | 11/1966 | McHattie.................... | 260/256.4 C |
| 3,591,589 | 7/1971 | Kim et al..................... | 260/256.4 C |
| 3,862,188 | 1/1975 | Milzner et al............... | 260/251 |

FOREIGN PATENTS OR APPLICATIONS

| | | |
|---|---|---|
| 1,223,686 | 3/1971 | United Kingdom |
| 1,182,584 | 2/1970 | United Kingdom |
| 509,039 | 8/1971 | Switzerland |
| 83,560 | 4/1954 | Norway |
| 2,144,392 | 3/1973 | Germany |

OTHER PUBLICATIONS

Koppel, et al., "Journ. of Org. Chem.," Vol. 26, 1961, pp. 792–803.

Park, et al., "Journ. of Org. Chem.," Vol. 27, 1962, pp. 1462–1463.

Brown, *The Pyrimidine*, 1962, pp. 25.

Brown, "Australian J. Chem.," Vol. 18, 1965, pp. 559–568.

Brown, *The Pyrimidines*, Supplement I, 1970, pp. 149–150.

Snell, et al., "J. Chem. Soc.," (c), 1968, pp. 2358–2367.

*Primary Examiner*—Donald G. Daus
*Assistant Examiner*—James H. Turnipseed
*Attorney, Agent, or Firm*—Gerald D. Sharkin; Richard E. Vila

[57] ABSTRACT

The present invention concerns novel 4-hydroxypyrimidine derivatives of the formula:

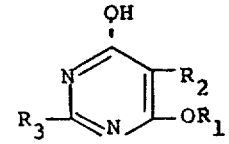

wherein $R_1$ is a substituent, e.g., alkyl, $R_2$ is hydrogen or a substituent, e.g., alkyl $R_3$ is amino unsubstituted or substituted by alkyl, a nitrogen heterocycle, alkoxy or alkylthio, which are used as intermediates in the production of useful insecticides.

12 Claims, No Drawings

SUBSTITUTED 6-HYDROXY PYRIMIDINES

The present invention relates to 4-hydroxy-pyrimidine derivatives which are useful as intermediates in the production of useful insecticides.

Accordingly, the present invention relates to compounds of formula I,

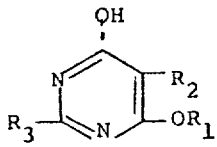
I wherein $R_1$ is alkyl ($C_1$-$C_6$) or cycloalkyl ($C_3$-$C_8$),
$R_2$ is hydrogen, alkyl ($C_1$-$C_6$) or alkenyl-($C_2$-$C_6$) and
$R_3$ is a radical —$NR_4R_5$
   wherein $R_4$ and $R_5$ are either each, independently, hydrogen or alkyl ($C_1$-$C_6$) or together with the nitrogen atom to which they are bound form a 5 or 6 membered heterocyclic ring,
or alkoxy or alkylthio ($C_1$-$C_6$).

When $R_4$ or $R_5$ is a 5 or 6 membered heterocycle, this preferably contains 1 or 2 hetero atoms, which apart from the nitrogen atom may be oxygen or a further nitrogen atom and is preferably piperidino, morpholino or pyrrolidino.

The present invention also provides a process for the production of a compound of formula I, which comprises a. reacting a compound of formula II,

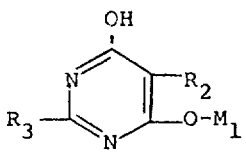
II wherein
$R_2$ and $R_3$ are as defined above and
$M_1$ is hydrogen or a cation, preferably a sodium or potassium cation,
with an equivalent of an alkylating reagent of formula III,

III wherein
$R_1$ is as defined above and
Ar is phenyl or tosyl, preferably in the presence of alkali,
or b. reacting a compound of formula II with a dialkyl sulphate of formula IV, $$(R_nO)_2SO_2 \quad \text{IV}$$

wherein $R_n$ is alkyl ($C_1$-$C_3$),
under alkylation conditions, i.e., in the presence of alkali in a pH range of 7.5 to 8.5, to produce a compound of formula Ia,

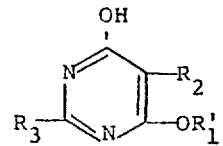
Ia wherein
$R_2$ and $R_3$ are as defined above and
$R_1'$ is alkyl ($C_1$-$C_3$).

When $R_3$ of formula I is a primary or secondary amino function, the amino function is preferably protected against alkylation with a suitable protecting group.

The production of the compounds of formula I may be effected as follows:

In accordance with the process variant (a), the compound of formula II is reacted with an equivalent of the compound of formula III, in an appropriate solvent such as for example the alcohol which corresponds to the alkylation radical $R_1$, preferably in the presence of alkali, conveniently in aqueous alkali and optionally with heating.

Working up is effected in conventional manner.

In accordance with process variant (b), the compound of formula II is reacted with an equivalent of dialkyl sulphate of formula IV, in an appropriate solvent such as for example alcohol, preferably in aqueous alkaline solution, especially in sodium hydroxide solution (2N), optionally with heating, in a pH range of 7.5 to 8.5. In order to complete the reaction, the reaction mixture may be stirred over a period of, for example, several hours and with heating, especially when $R_n$ is ethyl or propyl. The pH value is preferably kept inbetween the above-mentioned range by the addition of alkali.

Working up is effected in conventional manner.

The compounds of formula I, are colorless crystalline substances which may, for example, be characterized by their melting points.

Compounds of formula I, may exist either in free base or acid addition salt forms. Free base forms may be produced from acid addition salt forms in manner known per se and vice versa.

The compounds of formulae II, III and IV are known or may be produced in accordance with known processes or in analogy with processes known per se.

The compounds of formula II, wherein $R_3$ is alkylthio may, for example, be produced in accordance with conventional processes by alkylation of 2-thiobarbituric acid or its derivatives substituted by $R_2$ in the 5-position. The precautions recommended in connection with thiol compounds are to be taken.

The compounds of formula I, are useful in the production of useful insecticides of formula V,

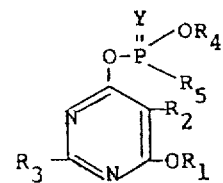
V wherein
$R_1$, $R_2$ and $R_3$ are as defined above,
$R_4$ is alkyl of 1 to 6 carbon atoms, $R_5$ is alkoxy of 1 to 6 carbon atoms, alkyl-thio of 1 to 6 carbon atoms, amino or amino mono- or disubstituted by alkyl of 1 to 6 carbon atoms and Y is oxygen or sulphur, by a process which comprises reacting the compound of formula I or a metal, e.g., sodium or potassium, salt thereof, with a compound of formula VI,

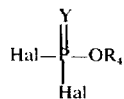            VI wherein $R_4$ and Y are as defined above and

Hal is chlorine or bromine and reacting the resulting compound with a compound of formula VII, $M_2R_5$            VII wherein $R_5$ is as defined above and $M_2$ is hydrogen or when $R_5$ is alkoxy or alkylthio, a metal cation.

The insecticides of formula V are useful particularly in animal buildings, e.g., stables, inhabited rooms, e.g., cellars and attics, and in plant loci.

For the above-mentioned use, the amount of the compound to be applied will vary depending on the particular compound employed, the mode of application, ambient conditions and the effect desired. With regard to plant protection, in general an indicated amount to be applied to a plant locus is between 0.01 and 5 kg/hectare.

The compounds may be employed as a composition with insecticidal carriers and diluents in solid or liquid form, e.g., spraying and dusting powders, pellets, strewing granulates, pastes, spraying liquids and aerosols.

Solid forms may include carriers such as diatomaceous earth, talc, kaolinite, attapulgite, pyrophyllite, artifical mineral fillers based on $SiO_2$ and silicates, lime, sodium sulphate decahydrate and plant material carriers, such as ground walnutshell. Adjuvants such as surfactants, including wetting and dispersing agents, e.g., sodium-lauryl sulphate, sodium dodecyl benzene-sulphonate, condensation products from naphthalene sulphonate and formaldehyde, polyglycol ether and lignin derivatives such as sulphite liquor, may also be included in the case of wettable powders to be applied as a water suspension. Granulates are produced by coating or impregnating granular carrier materials such as pumice, limestone, attapulgite and kaolinite with the compounds.

Liquid forms may include non-phytotoxic diluents, such as alcohols, glycols, glycolic ethers, aliphatic and aromatic hydrocarbons, e.g., xylene, alkyl napthalenes and other petroleum distillates, and ketones, e.g., cyclohexanone and isophorone. Adjuvants, such as surface active agents, e.g., wetting and emulsifying agents, such as polyglycol ether formed by the reaction of an alkylene oxide with high molecular weight alcohols, mercaptans or alkyl phenols, and/or alkyl benzene sulphonates, may be included in emulsion concentrate forms.

Aside from the carriers, diluents and adjuvants already mentioned, adjuvants such as stabilizing agents, desactivators (for solid forms with carriers having an active surface), agents for improving adhesiveness to the surface treated, anticorrosives, defoaming agents and pigments may also be included.

Concentrate forms of composition generally contain between 1 and 90 % preferably between 5 and 50 % by weight of active compound.

Application forms of composition generally contain between 0.02 and 90 %, preferably between 0.1 and 20 % by weight of active compound.

Examples of concentrate and application forms of composition will now be described:

a. Emulsifiable concentrate 25 parts by weight of a compound of formula V are mixed with 20 parts by weight of isooctylphenyldeca-glycol ether, 5 parts by weight of the calcium salt of an alkyl aryl sulphonate and 50 parts by weight of xylene, whereby a clear solution is obtained which may be readily emulsified in water. The concentrate is diluted with water to the desired concentration for use.

b. Emulsifiable concentrate 25 parts by weight of a compound of formula V are mixed with 35 parts by weight of isooctylphenylocta-glycol ether, 5 parts by weight of the calcium salt of an alkyl aryl sulphonate and 45 parts by weight of an aromatic petroleum fraction having a boiling point of 210° to 280° ($D_{20}$ : 0.92). The concentrate is diluted with water to the desired concentration for use.

c. Spraying and dusting powder application form 25 parts by weight of a compound of formula V, 2 parts by weight of sodium-lauryl sulphate, and 3 parts by weight of sodium lignin sulphonate are mixed with 70 parts by weight of diatomaceous earth and ground until the particles have obtained a size of 10 $\mu$ as an average.

The following Examples illustrate the production of the compounds according to the invention but without in any way limiting the invention. Where temperature is referred to, this is in °C.

EXAMPLE 1

2-Diethylamino-4-methoxy-6-hydroxy-pyrimidine 500 cc of sodium hydroxide solution 1N are added while stirring to 91.5 g (0.5 mol) of 2-diethylamino-4,6-dihydroxy-pyrimidine. The solution is stirred at 50° for a short period and then cooled to 20°. 63 g (0.5 mol) of dimethyl sulphate are added dropwise, over the course of 1 hour, to the clear solution; by further addition of 1N sodium hydroxide solution the pH value is kept between 7.5 and 8. A total of approximately 100 cc of 1N sodium hydroxide solution is additionally required. The mixture is stirred for a further 5 hours at room temperature and the precipitated crystals are filtered off at 5°; then they are washed with water. The crystalline product is subsequently triturated with 1500 cc of carbon tetrachloride by means of a vibration mixer. The undissolved parts are suction filtered and the carbon tetrachloride solution is then concentrated by evaporation, whereupon crystallization commences; 200 cc of petroleum ether are then added.

The mixture is suction filtered, washed with petroleum ether and dried at 80° in a high vacuum. Optionally it may be recrystallized from benzene. M.P.: 165°-166°.

Analysis: $C_9H_{15}N_3O_2$. Molecular weight: 197.2. Calc.: C, 54.8 %; H, 7.7 %; N, 21.3 %; O, 16.2 %. Found: C, 54.5 %; H, 7.4 %; N, 21.1 %; O, 16.3 %.

The following compounds of general formula I may be produced in analogous manner to that described in Example 1:

EXAMPLE 2

2-Dimethylamino-4-methoxy-6-hydroxypyrimidine

M.P.: 215°–216°.

Analysis: $C_7H_{11}N_3O_2$. Molecular weight: 169.2. Calc.: C, 49.7 %; H, 6.6 %; N, 24.8 %; O, 18.9 %. Found: C, 49.7 %; H, 6.4 %; N, 24.7 %; O, 19.0 %.

EXAMPLE 3

2-Di-n.propylamino-4methoxy-6-hydroxypyrimidine

M.P.: 116°–117°

Analysis: $C_{11}H_{19}N_3O_2$. Molecular weight: 225.3. Calc.: C, 58.6 %; H, 8.5 %; N, 18.7 %; O, 14.2 %. Found: C, 59.3 %; H, 8.6 %; N, 18.2 %; O, 14.4 %.

EXAMPLE 4

2-Dimethylamino-4-ethoxy-6-hydroxypyrimidine 155.2 g (1 mol) of 2-dimethylamino-4,6-dihydroxypyrimidine are added while stirring to 1000 cc of 1N sodium hydroxide solution 1N and the mixture is heated to 50° over a short period. 170 g (1.1 mol) of diethyl sulphate are subsequently added dropwise, over the course of 2 hours, at 40°–45°. During the dropwise addition the pH value is kept at between 7.5 and 8.0 by further addition of 1N sodium hydroxide solution. Approximately 500 cc of 1N sodium hydroxide solution are additionally required. The mixture is stirred at 40° for 6 hours, filtered off, washed with a small amount of water and dried at 90° in a high vacuum. The compound may be recrystallized from benzene. M.P. 194°–195°. The aqueous phase may be extracted with chloroform in order to obtain better yields. The chloroform solution is dried with sodium sulphate and after evaporation crystals are obtained which may be recrystallized from benzene.

Analysis: $C_8H_{13}N_3O_2$. Molecular weight: 183.2. Calc.: C, 52.4 %; H, 7.2 %; N, 22.9 %; O, 17.5 %. Found: C, 52.4 %; H, 7.0 %; N, 22.9 %; O, 17.8 %.

The following compounds of general formula I may be produced in analogous manner to that described in Example 4:

EXAMPLE 5

2-Diethylamino-4-ethoxy-6-hydroxypyrimidine

M.P.: 144°–145°

Analysis: $C_{10}H_{17}N_3O_2$. Molecular weight: 211.26. Calc.: C, 57.0 %; H, 8.1 %; N, 19.8 %; O, 15.1 %. Found: C, 57.5 %; H, 8.2 %; N, 19.8 %; O, 15.3 %.

EXAMPLE 6

2-Di-n.propylamino-4-ethoxy-6-hydroxypyrimidine

M.P.: 132°–133°

Analysis: $C_{12}H_{21}N_3O_2$. Molecular weight: 239.32. Calc.: C, 60.2 %; H, 8.8 %; O, 13.4 %; N, 17.6 %. Found: C, 60.1 %; H, 8.6 %; O, 13.5 %; N, 17.4 %.

EXAMPLE 7

2-Methoxy-4-ethoxy-6-hydroxypyrimidine 14.2 g (0.1 mol) of 2-methoxy-4,6-dihydroxypyrimidine are added while stirring to 50 cc of 2N sodium hydroxide solution 2N and the mixture is stirred for half an hour with heating to 50°. 17.0 g (0.11 mol) of diethyl sulphate are subsequently added dropwise, over the course of 20 minutes and with stirring; by adding 2N sodium hydroxide solution the pH value should, if possible, be kept at between 8 and 8.2. The mixture is then stirred at 50°, 2N sodium hydroxide solution is added from time to time until the pH remains constant (after approximately 3 hours). The reaction mixture is subsequently cooled to 0°, the precipitate is suction filtered and washed with a small quantity of ethanol. After drying in a high vacuum at 80°, the substance has a M.P. of 192°–194°.

Analysis: $C_7H_{10}N_2O_3$. Molecular weight: 170.2. Calc.: C, 49.4 %; H, 5.9 %; N, 16.5 %; O, 28.2 %. Found: C, 49.5 %; H, 5.8 %; N, 16.1 %; O, 27.9 %.

EXAMPLE 8

2-Methoxy-4-methoxy-6-hydroxypyrimidine 142 g (1 mol) of 2-methoxy-4,6-dihydroxypyrimidine are added while stirring to 500 cc of sodium hydroxide solution 2N and the mixture is stirred at 50° for 1 hour. Subsequently it is cooled to room temperature and 139 g (1.1 mol) of dimethyl sulphate are added dropwise while stirring; by the addition of 2N sodium hydroxide solution the pH value is kept at between 8.0 and 8.2. The mixture is stirred at 50° for a further 2 hours, cooled to room temperature and extracted with chloroform. After drying the chloroform phase over sodium sulphate the solvent is evaporated in a vacuum. A white powder is obtained. After decomposition with ether/chloroform (1:1), the substance has a M.P. of 197°–201°.

Analysis: $C_6H_8N_2O_3$. Molecular weight: 156.1. Calc.: C, 46.1 %; H, 5.1 %; N, 17.9 %; O, 30.8 %. Found: C, 46.3 %; H, 5.0 %; N, 17.7 %; O, 31.0 %.

EXAMPLE 9

2-Methylthio-4-ethoxy-6-hydroxypyrimidine 31.6 g (0.2 mol) of 2-methylthio-4,6-dihydroxypyrimidine are added, while stirring well, to 100 cc of 2N sodium hydroxide solution 2N and the mixture is stirred at 50° for half an hour. 34.0 g (0.22 mol) of diethyl sulphate are then added dropwise and with stirring, at 50°; by the addition of 2N sodium sulphate the pH value is kept at between 8 and 8.2. Towards the end of the dropwise addition a precipitate is obtained. The mixture is subsequently stirred at 50° for 1 further hour, cooled to 0° and filtered. The precipitate is washed with cold ethanol, then with ether and dried in a high vacuum at 80°. The obtained white powder has a M.P. of 185°–187°.

Analysis: $C_7H_{10}N_2O_2S$. Molecular weight: 186.2. Calc.: C, 45.1 %; H, 5.4 %; N, 15.0 %; O, 17.2 %; S, 17.2 %. Found: C, 44.8 %; H, 5.4 %; N, 15.0 %; O, 17.6 %; S, 17.1 %.

EXAMPLE 10

2-Methylthio-4-methoxy-6-hydroxypyrimidine 15.8 g (0.2 mol) of 2-methylthio-4,6-dihydroxypyrimidine are added while stirring well, to 100 cc of 2N sodium hydroxide solution and the mixture is stirred at 50° for half an hour. The mixture is subsequently cooled to room temperature and 13.9 g (0.11 mol) of dimethyl sulphate are added dropwise, while stirring; by the addition of sodium hydroxide solution 2N the pH value is kept at between 8 and 8.2. After the dropwise addition a precipitate is obtained. The mixture is stirred at 50° for a further 2½ hours, whereby the pH value is kept at between 8 and 8.3, then cooled to 0° and filtered. The obtained white powder has an M.P. of 193°–195°.

Analysis: $C_6H_8N_2O_2S$. Molecular weight: 172.2. Calc.: C, 41.9 %; H, 4.7 %; N, 16.3 %; O, 18.6 %; S, 18.6 %. Found: C, 41.7 %; H, 4.6 %; N, 16.5 %; O, 18.8 %; S, 18.4 %.

EXAMPLE 11

2-Dimethylamino-4-n-propoxy-6-hydroxy-pyrimidine 124 g (0.8 mol) of 2-dimethylamino-4,6-dihydroxypyrimidine are stirred with 800 cc of 1N sodium hydroxide solution at 60° for 1 hour. 171 g (0.8 mol) of p-toluenesulphonic acid-n-propyl ester are added dropwise at 90° over the course of 1 hour and the pH is kept at 8–8.5 by the dropwise addition of 1N sodium hydroxide solution. The mixture is stirred at 90° for 16 hours, cooled to 5°, neutralized with glacial acetic acid and allowed to stand at room temperature for 6 hours. The precipitated crystals are subsequently filtered by suction, washed with water, dissolved in approximately 700 cc of chloroform, dried over sodium sulphate and evaporated to dryness in a vacuum. The residue is decomposed with 500 cc of petroleum ether, filtered by suction and recrystallized from benzene, washed with petroleum ether and dried at 60° in a high vacuum. M.P.: 194°–195°.

Analysis: $C_9H_{15}N_3O_2$. Molecular weight: 197.24. Calc.: C, 54.8 %; H, 7.7 %; N, 21.3 %. Found: C, 54.5 %; H, 7.7 %; N, 21.3 %.

The starting materials of formula II, wherein $R_3$ is alkylthio and $M_1$ is hydrogen, may be produced in accordance with the following Example:

EXAMPLE 12

2-Methylthio-4,6-dihydroxypyrimidine

The following process is to be effected only with gas-mask and gloves.

600 g (4.15 mols) of thiobarbituric acid are dissolved in 8 l of 2N sodium hydroxide solution. 523 g (4.15 mols) of dimethyl sulphate are then added dropwise, while stirring, at room temperature, over the course of 15 minutes, whereupon the temperature rises to approximately 38°. The solution is allowed to react for 3 hours without cooling; the reaction mixture is then boiled for approximately 10 minutes, treated with charcoal and after cooling, the pH value is adjusted to 1 with 900 cc of concentrated hydrochloric acid. The compound crystallizes as colorless needles while cooling with ice. Filtration is effected and the precipitate is washed with approximately 2 l of ice-cold water.

Analysis: $C_5H_6N_2O_2S$. Molecular weight: 158.2. Calc.: C, 38.0 %; H, 3.8 %; N, 17.7 %; S, 20.3 %; O, 20.3 %. Found: C, 38.8 %; H, 3.8 %; N, 17.6 %; S, 20.2 %; O, 20.1 %.

What is claimed is:

1. A compound of the formula:

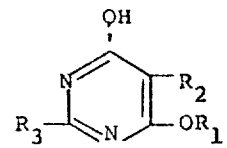

wherein
  $R_1$ is alkyl ($C_1$–$C_6$) or cycloalkyl ($C_3$–$C_8$),
  $R_2$ is hydrogen, alkyl ($C_1$–$C_6$) or alkenyl-($C_2$–$C_6$) and
  $R_3$ is a radical —$NR_4R_5$
    wherein $R_4$ and $R_5$ are either each, independently, hydrogen or alkyl ($C_1$–$C_6$) or together with the nitrogen atom to which they are bound form piperidino, morpholino or pyrrolidino,
  or alkoxy or alkylthio ($C_1$–$C_6$).

2. The compound of claim 1, which is 2-diethylamino-4-methoxy-6-hydroxy-pyrimidine.

3. The compound of claim 1, which is 2-dimethylamino-4-methoxy-6-hydroxy-pyrimidine.

4. The compound of claim 1, which is 2-di-n.propylamino-4-methoxy-6-hydroxy-pyrimidine.

5. The compound of claim 1, which is 2-dimethylamino-4-ethoxy-6-hydroxy-pyrimidine.

6. The compound of claim 1, which is 2-diethylamino-4-ethoxy-6-hydroxy-pyrimidine.

7. The compound of claim 1, which is 2-di-n.propylamino-4-ethoxy-6-hydroxy-pyrimidine.

8. The compound of claim 1, which is 2-methoxy-4-ethoxy-6-hydroxypyrimidine.

9. The compound of claim 1, which is 2-methoxy-4-methoxy-6-hydroxypyrimidine.

10. The compound of claim 1, which is 2-methylthio-4-ethoxy-6-hydroxypyrimidine.

11. The compound of claim 1, which is 2-methylthio-4-methoxy-6-hydroxypyrimidine.

12. The compound of claim 1, which is 2-dimethylamino-4-n-propoxy-6-hydroxypyrimidine.

* * * * *